(12) United States Patent
Boehm et al.

(10) Patent No.: US 9,078,466 B2
(45) Date of Patent: *Jul. 14, 2015

(54) COMPOSITION TO TREAT AND/OR PREVENT GASTROINTESTINAL INFECTION

(75) Inventors: Gunther Boehm, Echzell (DE); Jaochim Schmitt, Hosbach (DE); Gilda Georgi, Hosbach (DE); Marco Euler, Wolfersheim (DE)

(73) Assignee: N. V. NUTRICIA, Zoetermeer (NL)

( * ) Notice: Subject to any disclaimer, the term of this patent is extended or adjusted under 35 U.S.C. 154(b) by 822 days.

This patent is subject to a terminal disclaimer.

(21) Appl. No.: 12/311,694

(22) PCT Filed: Sep. 20, 2007

(86) PCT No.: PCT/EP2007/008179
§ 371 (c)(1),
(2), (4) Date: Jan. 11, 2010

(87) PCT Pub. No.: WO2008/043424
PCT Pub. Date: Apr. 17, 2008

(65) Prior Publication Data
US 2010/0120676 A1     May 13, 2010

(30) Foreign Application Priority Data

Oct. 12, 2006  (EP) .................................... 06021422

(51) Int. Cl.
*A61K 36/48*    (2006.01)
*A61K 36/00*    (2006.01)
*A61K 35/20*    (2006.01)
*A23L 1/305*    (2006.01)

(52) U.S. Cl.
CPC ............. *A23L 1/3056* (2013.01); *A23L 1/3053* (2013.01); *A23L 1/3055* (2013.01); *A61K 35/20* (2013.01); *A61K 36/48* (2013.01)

(58) Field of Classification Search
None
See application file for complete search history.

(56) References Cited

U.S. PATENT DOCUMENTS 5,660,842 A * 8/1997 Petschow ...................... 424/405

FOREIGN PATENT DOCUMENTS

| CN | 1579198 A | 2/2005 | |
|---|---|---|---|
| DE | 103 17 935 A1 * | 11/2004 | ............. A61K 38/17 |
| DE | 10317935 A1 | 11/2004 | |
| JP | 2001335504 A | 12/2001 | |
| WO | WO 96/24368 A | 8/1996 | |
| WO | 00/54603 A1 | 9/2000 | |
| WO | WO 2005/060952 A | 7/2005 | |

OTHER PUBLICATIONS

Shabo et al.; Int. J. Dis Human Dev.; (2005); 4(2); 67-70.*
Stromqvist et al.; J. Pediatric Gastroenterology and Nutrition; 21:288-296 (1995).*
Ho et al.; J. Food Biochem.; 30 (2006), pp. 21-34.*
Google search results; 2 pp.; downloaded Aug. 14, 2014.*
Shabo, Yosef et al: "Etiology of autism and camel milk and therapy" Int J Dis Human Dev, vol. 4, No. 2, 2005, pp. 67-70, XP001249166, p. 68, col. 2, p. 69, col. 1, paragraph 7.
DE 103 17 935 A1 (S K ENTPR GMBH [DE]) Nov. 4, 2004.
Stromqvist Mats et al: "Human milk kappa-casein and inhibition of *Helicobacter* adhesion to human gastric mucosa" Journal of Pediatric Gastroenterology and Nutrition, vol. 21, 1995, pp. 288-296, XP009080063 abstract.
Chinese Office Action in corresponding Chinese Application No. 200780037951.4, dated Aug. 5, 2011 with English translation.

* cited by examiner

*Primary Examiner* — Jeffrey T Palenik
(74) *Attorney, Agent, or Firm* — Bacon & Thomas, PLLC

(57) ABSTRACT

The invention relates to a composition for the treatment and/or prevention of infection by gastrointestinal pathogens, in particular *Helicobacter pylori* and/or a disease associated with infection by said gastrointestinal pathogen in mammals.

6 Claims, No Drawings

COMPOSITION TO TREAT AND/OR PREVENT GASTROINTESTINAL INFECTION

CROSS REFERENCE TO RELATED APPLICATIONS

This application is a 371 of International Application No. PCT/EP2007/008179, filed on Sep. 20, 2007, which claims benefit to European Application No. 06021422.8, filed on Oct. 12, 2006, the entire contents of which are incorporated herein by reference.

FIELD OF THE INVENTION

The present invention relates to the treatment and/or prevention of infection by gastrointestinal pathogens, particularly Helicobacter pylori.

BACKGROUND OF THE INVENTION

Gastrointestinal infections are a major problem in many humans, and particularly in infant and patients with an impaired immune system or gastrointestinal diseases. The resulting diseases can be life threatening. Gastrointestinal infections are often caused by Escherichia coli, Salmonella, Campylobacter, Clostridium, Enterobacter and Helicobacter, e.g. Helicobacter pylori.

Helicobacter pylori (H. pylori) is a Gram-negative, microaerophilic flagellated bacterium that colonizes the gastric mucosa of humans upon infection. H. pylori infection has been associated with severe gastric diseases, such as gastritis, peptic ulcer and gastric cancer. H. pylori has been classified as a Group I carcinogen by the World Health Organisation. H. pylori infection is usually chronic and mostly not heals without specific therapy.

H. pylori infection is mainly acquired in early childhood. Most children are infected during the first 5 years of life [Vandenplas Y, Curr Opin Infect Dis 2001; 14(3): 315-321]. By the age of 10, overall prevalence is more than 75% in developing countries, whereas 10% are infected in developed countries, but prevalence can rise to 30-40% in children from lower socio-economic groups.

The mechanism of H. pylori transmission is not fully understood yet and needs further elucidation. Under current discussion are oral-oral, gastro-oral (via emesis), faecal-oral modes, drinking water supply (in developing countries) or even improperly cleaned endoscopic equipment.

Treatment to eradicate H. pylori infection requires three to four medications. The Canadian and most European H. pylori study groups now recommend (in adults) a triple regimen: a twice-daily dose of proton pump inhibitor in combination with two antibiotics, e.g. clarithromycin and amoxicillin, for 1-2 weeks. Treatment is very expensive and there is also the risk of increasing antibiotic resistance in bacterial strains and re-infection following unsuccessful therapy. Treatment of children may be the most cost effective method of reducing the incidence of infection and the morbidity and mortality associated with H. pylori related diseases. So far there are no guidelines on the need to treat children. A human vaccine is not yet available. Prophylaxis and therapeutic vaccination have been successful in animal models, but the translation to a human vaccine remains difficult, in part because the immunology of the stomach is still poorly understood.

With regard to the problems of treatment by antibiotics and prophylaxis by vaccination, the adhesion of H. pylori to the gastric mucosa should be prevented. Without adhesion of the bacteria, the risk of a related inflammation resulting in gastritis or possibly in cancer can be minimised. Dietary modulation (probiotics) has proven to be useful in supporting H. pylori infection treatment or prophylaxis in vivo and in vitro [Michetti P et al., Digestion 1999; 60(3): 203-209 and Midolo P D et al., J Appl Bacteriol 1995; 79(4): 475-479].

WO 94/18986 relates to the use of di- or oligosaccharide glycosides containing at least one terminal L-fucose unit for the preparation of pharmaceutical compositions for the treatment or prophylaxis in humans of conditions involving infection by Helicobacter pylori in the human gastric mucosa.

EP 0713700 describes a method for inhibiting Helicobacter by administering C8-C16 monoglycerides of fatty acids or lauric acid. The monoglycerides and/or lauric acid are conveniently administered via a nutritional composition.

EP 1178104 relates to a nutritional composition comprising a specific essential oil and/or specific pure compound isolated from the essential oil for prevention or treatment of infection by a Helicobacter-like organism. The nutritional composition may also contain a source of carbohydrates, a source of fat and/or a source of a dietary protein pea protein being one of them.

JP 2005255679 describes a polypeptide obtained by treating butter milk with a protease having not only adhesion inhibitory effect of Helicobacter pylori to gastric mucosa but also the effect of debonding Helicobacter pylori off the gastric mucosa of Helicobacter pylori carriers.

JP 2001335504 describes a proliferation inhibitor of Helicobacter pylori comprises a soybean protein enzymic hydrolysate as an active ingredient.

DE 10317935 describes the use of casein to prepare a composition for prevention or treatment of Helicobacter infection and for preventing diseases caused by Helicobacter infection.

SUMMARY OF THE INVENTION

The present invention relates to the use of a composition comprising a pea protein hydrolysate, intact pea protein and/or a camel milk protein hydrolysate for the treatment and/or prevention of infection by gastrointestinal pathogens and/or a disease associated with infection by said gastrointestinal pathogen in mammals, particularly infections by gastrointestinal pathogen selected from the group consisting of Helicobacter, Escherichia coli, Salmonella, Campylobacter, Clostridium and Enterobacter. The invention relates furthermore to the use of a pea protein hydrolysate, intact pea protein and/or a camel milk protein hydrolysate for the preparation of a composition for the treatment and/or prevention of the infection or disease, respectively, specified above.

The present inventors have found that pea protein hydrolysate, intact pea protein and camel casein hydrolysate (hereinafter collectively referred to as "present protein component") are able to inhibit the adhesion of H. pylori to gastric mucosa cells. The terms pea protein hydrolysate and camel casein hydrolysate (hereinafter collectively referred to as "present protein hydrolysate component) as used in the present invention refer to peptides thereof and/or glycoconjugates thereof, but preferably refers to peptides obtained by hydrolysis of pea protein and/or obtained by hydrolysis of camel casein. The inhibition of adhesion makes these protein components particularly suitable for the use in a method for the treatment and/or prevention of Helicobacter infection.

Particularly good results have been achieved with pea protein hydrolysates. Preferably the pea protein hydrolysate has been obtained by hydrolysis of pea protein isolate. Pea protein isolate preferably contains at least 75 wt. % pea protein per 100 gram pea protein isolate.

The present protein component and in particular the present protein hydrolysate component can be easily added to infant formulas, toddler products, and products for young people. The easy and safe use of this protein component makes the invention of particular importance, as the problems of side effect normally encountered with medicaments and the costly multi-medicine therapies are circumvented. The present protein component can also be suitably used by adults.

An additional advantage of the use of the present protein component, particularly the present pea protein hydrolysate, is that it is preferably and normally readily soluble in water, e.g. making it particularly suitable for use in a liquid nutritional product. This brings the advantage that the present anti-infective protein component does not have to be administered separately (e.g. to infants), but can be co-administered within a nutritional composition.

Because increased duration of exclusive breastfeeding in infancy may have a long-term protective effect against chronic *H. pylori* infection and hence the risk of gastric carcinoma (J Pediatr Gastroenterol Nutr. 2005 November; 41(5): 617-20), it is particularly desirable to also protect infants which receive infant formula against *H. pylori* infection. It was surprisingly found that the present protein component (particularly pea protein hydrolysate) can be used to reduce and/or prevent *H. pylori* infection.

In a further embodiment the present protein component can be suitably used for prophylaxis of gastrointestinal pathogenic infection for avoiding a re-infection with the gastrointestinal pathogen after antibiotics treatment, particularly prophylaxis of *H. pylori* infection for avoiding a re-infection with *H. pylori* after antibiotics treatment As *H. pylori* infection in early life has been described to increase the risk for development of intestinal carcinoma, particularly gastric carcinoma, gastritis and peptic ulcer, the present invention also provides a method for the prevention of these diseases by administering pea protein hydrolysate and/or camel milk protein hydrolysate.

DETAILED DESCRIPTION OF PREFERRED EMBODIMENTS

The present invention provides the use of a composition comprising pea protein hydrolysate, intact pea protein and/or camel milk protein hydrolysate for the preparation of a composition for the treatment and/or prevention of infection by gastrointestinal pathogens and/or a disease associated with infection by said gastrointestinal pathogens in mammals.

The present invention also provides a method for the treatment and/or prevention of infection by gastrointestinal pathogens and/or a disease associated with infection by gastrointestinal pathogens in mammals, said method comprising administering pea protein hydrolysate, intact pea protein and/or camel milk protein hydrolysate to said mammal. Preferably the mammal is an infant or child, more preferably an infant with the age between 0 and 5 years and/or a patient suffering from gastroduodenal diseases.

In a further aspect the present invention provides a composition containing a lipid constituent proving 5 to 50% of the total calories, a protein constituent providing 5 to 50% of the total calories and a carbohydrate constituent providing 15 to 90% of the total calories. Said composition is characterized in that the protein constituent comprises: (i) at least one protein source selected from the group consisting of a pea protein hydrolysate, intact pea protein and a camel milk protein hydrolysate; and (ii) at least one nitrogen source selected from the group of milk proteins, milk protein hydrolysate, egg proteins, egg protein hydrolysate, soy protein, soy protein hydrolysate, wheat protein, wheat protein, hydrolysate, rice protein, rice protein hydrolysate, free amino acids and mixtures thereof. The above used terms "lipid constituent, protein constituent and fat constituent" designate the sum of all lipid ingredients, protein ingredients or carbohydrate ingredients, respectively, present in the composition.

In a still further aspect the present invention provides the use of this composition for the treatment and/or prevention of infection by gastrointestinal pathogens and/or a disease associated with infection by said gastrointestinal pathogen in mammals.

A further subject of the present invention is directed to Pea protein hydrolysate, intact pea protein and/or camel milk protein hydrolysate for the treatment and/or prevention of infection by gastrointestinal pathogens and/or a disease associated with infection by said gastrointestinal pathogen in mammals.

Protein

The present invention provides a composition containing pea protein hydrolysate, intact pea protein and/or camel milk protein hydrolysate, and the use of such composition for the present treatments.

Camel casein hydrolysate was also found to be particularly effective. Hence, in one embodiment the present composition preferably contains camel milk protein hydrolysate, preferably camel casein hydrolysate.

The preferred present protein hydrolysate component is pea protein hydrolysate.

By gel electrophoresis (LDS-PAGE with coomassie and silver staining) and MALDI mass spectrometry the molecular weight range of the most effective anti-*helicobacter* adhesive peptides and/or glycoconjugates in the present protein hydrolysate component is 300-12000 Da, preferably 2200-6000 Da. Hence the present protein hydrolysate component preferably contains at least 1 wt. % peptides and/or glycoconjugates (preferably peptides) with a molecular weight of 300 to 12000 Da based on total weight of the present protein hydrolysate, preferably at least 5 wt. %, more preferably at least 50 wt. %, most preferably at least 75 wt. %. More preferably the present protein hydrolysate component comprises at least 1 wt. % peptides and/or glycoconjugates (preferably peptides) with a molecular weight of 2200 to 6000 Da based on total weight of the present protein hydrolysate, preferably at least 5 wt. %, more preferably at least 50 wt. %, most preferably at least 75 wt. %.

The present protein component and in particular the present protein hydrolysate component are preferably administered in an amount of 0.1 to 100 grams per day, preferably in an amount of 0.5 to 10 grams per day.

Gastrointestinal Pathogens

The present method relates to the treatment and/or prevention of infection by gastrointestinal pathogens and/or a disease associated with infection by said gastrointestinal pathogen in mammals, particularly the treatment and/or prevention of infections by a gastrointestinal pathogen which is selected from the group consisting of *Helicobacter, Escherichia coli, Salmonella, Campylobacter, Clostridium* and *Enterobacter* and/or a disease associated with infection by said gastrointestinal pathogen in mammals.

The present invention particularly provides for the treatment and/or prevention of infections by *Helicobacter* and/or a disease associated with infection by *Helicobacter* in mammals. The *Helicobacter* is preferably selected from the group consisting of *Helicobacter pylori, Helicobacter bizzozeronii, H. salomonis, Helicobacter heilmannii* and *Helicobacter felis*. Preferably the present invention provides the treatment and/or prevention of infections by *Helicobacter pylori* (*H. pylori*) and/or a disease associated with infection by *Helicobacter pylori* in mammals.

Food Compositions

It was found that the present protein component and in particular the present protein hydrolysate component can be advantageously applied in food, such as baby food and clinical nutrition, particularly infant nutrition. The present nutritional composition preferably comprises a lipid constituent, a protein constituent and carbohydrate constituent.

Hence, the present invention also relates to a nutritional composition comprising the present protein component and preferably the present hydrolysate component and the use thereof in the present method, wherein the lipid constituent provides 5 to 50% of the total calories, the protein constituent provides 5 to 50% of the total calories, the carbohydrate constituent provides 15 to 90% of the total calories. The present composition is preferably used as an infant formula, wherein the lipid constituent provides 35 to 50% of the total calories, the protein constituent provides 7.5 to 12.5% of the total calories, and the carbohydrate constituent provides 40 to 55% of the total calories. For calculation of the % of total calories for the protein constituent, the total of proteins, peptides and amino acids needs to be taken.

Besides the present pea protein hydrolysate, intact pea protein and/or camel casein hydrolysate, the present composition preferably contains, an additional nitrogen source for nutritional purposes. The additional nitrogen source is preferably selected from the group consisting of protein, peptide, amino acids and mixtures thereof. Hence, in a preferred embodiment the protein component of the present composition comprises: (i) at least one protein source selected from the group consisting of pea protein hydrolysate, intact pea protein and camel milk protein hydrolysate; and (ii) at least nitrogen source selected from the group consisting of milk proteins, egg proteins, soy protein, wheat protein, rice protein, free amino acids and mixtures thereof. Preferably the present composition comprises (i) pea protein hydrolysate and (ii) at least one nitrogen source selected from the group of hydrolysed cows whey, non-hydrolysed cows whey, hydrolysed cows casein, non hydrolysed cows casein and non-hydrolysed soy protein.

When the present protein component and in particular the present protein hydrolysate component is administered in combination with an additional nitrogen source, the present composition preferably comprises between 1 and 50 wt. % of the present protein component and in particular of the present protein hydrolysate component based on total weight of protein.

A source of digestible carbohydrate may be added to the nutritional formula. The present composition preferably contains lactose.

In a preferred embodiment the anti-infective effect against the gastrointestinal pathogen of the present protein component and in particular the present protein hydrolysate component, preferably pea protein hydrolysate, is improved by co-administration of a soluble, non-digestible, fermentable oligosaccharide. Administration of these oligosaccharides stimulates the growth of lactic acid bacteria such as bifidobacteria and lactobacilli, preventing colonization and infection by gastrointestinal pathogens. Hence the present protein (hydrolysate) component and present oligosaccharide, act synergistically in this respect. The present oligosaccharide is preferably selected from the group consisting of galactooligosaccharides and fructooligosaccharides (e.g. inulin). Preferably at least 50 wt. % of the present oligosaccharides have a degree of polymerization of 2 to 60. In a particular preferred embodiment the present composition comprises at least galactooligosaccharides and fructooligosaccharides. The galactooligosaccharides preferably comprise saccharides with a DP of 2 to 10. The fructooligosaccharides preferably comprise saccharides with a DP of 2 to 60.

Stool irregularities (e.g. hard stools, insufficient stool volume, diarrhea) is a particular problem in many babies and ill subjects that have or are at risk of a *H. pylori* infection. These subjects often receive liquid foods. It was found that stool problems may be reduced by administering the present protein component in liquid foods which have an osmolality between 50 and 500 mOsm/kg, more preferably between 100 and 400 mOsm/kg. The prevention of stool problems is of particular importance when the present protein component is used together or after treatment with antibiotics. In view of the above, it is also important that the liquid food does not have an excessive caloric density, however still provides sufficient calories to feed the subject. Hence, the liquid food preferably has a caloric density between 0.1 and 2.5 kcal/ml, even more preferably a caloric density of between 0.5 and 1.5 kcal/ml, most preferably between 0.6 and 0.8 kcal/ml.

Application

The present invention provides a composition for and a method of the treatment and/or prevention of infection by gastrointestinal pathogens (particularly *H. pylori*) and/or a disease associated with infection by gastrointestinal pathogens (particularly *H. pylori*) in a human subject, said method comprising administering the present protein component and in particular the present protein hydrolysate component to the human subject. Diseases associated with infection by gastrointestinal pathogens in humans include persistent chronic gastritis, diarrhea, abdominal pain, ulcers and/or stomach cancer. Diseases associated with infection by *H. pylori* in humans include persistent chronic gastritis, ulcers and/or stomach cancer. The present invention also provides for the treatment and/or prevention of these diseases in human subjects at risk for, or in need for treatment thereof.

The present invention relates to the treatment and/or prevention in a mammal, preferably a human or a companion animal, more preferably humans. The present composition is advantageously administered to a) infants with the age between 0 and 5 years, preferably infants between 0 and 2 years and/or b) patients suffering from gastroduodenal diseases, particularly patients suffering from peptic ulcer.

The present invention is also particularly suitable for preventing re-infection with gastrointestinal pathogens, particularly *H. pylori*, after treatment of the mammal with one or more antibiotics.

EXAMPLES

Example 1

Anti-Infective Effect of Present Protein Hydrolysate Component

I. Preparation of Anti-Adhesive Peptides and Glycoconjugates by Enzymatic Hydrolysis Pea protein: Pea protein isolate (90% protein) was dispersed in distilled water to 2.5% (w/w). Hydrolysis was carried out at 50° C. for 180 min by adding trypsin and chymotrypsin with an enzyme to substrate ratio of 1:150 by weight for each protease. During hydrolysis pH was kept constant at pH 7.80 by addition of sodium hydroxide. Enzymes were inactivated by heating to 85° C. and maintenance of temperature between 85° C. to 80° C. for 5 min. The suspension was rapidly cooled on ice to room temperature and centrifuged afterwards at 3800×g for 15 min at 20° C. The supernatant was collected and freeze-dried.

Camel casein: Camel casein (85% protein) was dissolved in distilled water to 5% (w/w). Hydrolysis was carried out at 37° C. for 120 min by adding TPCK-treated trypsin with an enzyme to substrate ratio of 1:89 by weight. During hydrolysis the pH was kept constant at pH 7.00 by addition of sodium hydroxide. Hydrolysis was stopped by addition of hydrochloric acid to pH 4.60 and insoluble material removed by centrifugation at 3100×g for 20 min at 4° C. The supernatant was collected, neutralized to pH 6.90 with sodium chloride and freeze-dried.

II. Purification of Peptides and Glycoconjugates by Ultrafiltration (Example Peptides and Glycoconjugates from Pea Protein Isolate)

Pea protein hydrolysate was dissolved in distilled water to 1% w/v. Ultrafiltration was accomplished with Amicon® Ultra-15 or Centricon® Plus-20 centrifugal filter units (Millipore GmbH, Schwalbach, Germany). The devices used to obtain anti-*H. pylori* adhesion fractions have a nominal molecular weight cut-off (NMWCO) of 10 kDa for Amicon® Ultra-15 or 5 kDa NMWCO for Centricon® Plus-20. Filter units were prerinsed with distilled water by centrifugation at 4.500 rpm (4000×g) for 5 min at 10° C. (Beckman J2-21 centrifuge with rotor JS 7.5) to remove humectant (glycerol). This step was repeated once. The sample was centrifuged at 4.500 rpm (4000×g) for 30 min at 10° C. The filtrate was collected and the retentate diluted to approx. its original volume with distilled water and centrifugation was repeated. This step was done once more and the retentate was again diluted to its original volume. The retentate was then collected. Filtrate and retentate were freeze-dried.

III. In Situ Adherence Assay for *H. pylori*

The in situ test was performed essentially according to Falk et al. (Falk et al., Proc. Natl. Acad. Sci. 1993; 90:2035-2039). *H. pylori* type I strain G27 bacteria were used. To analyze the antiadhesive activity of peptides and glycoconjugates, aliquots (100-200 µl) of FITC-labeled *H. pylori* were pre-incubated with peptide and glycoconjugate) samples (0.01%-0.1% in blocking buffer) for 2 h at RT in the dark. FITC-labeled but untreated, i.e. without added peptides and glycoconjugates, aliquots of *H. pylori* served as control. The FITC-labeled bacterial suspension was diluted 20-fold in blocking buffer and 200 µl, respectively, were placed on a microscopic slide with the tissue section from human gastric mucosa and incubated. After washing bacterial adhesion was inspected by fluorescence microscopy. Comparable results were obtained when tissue section from human gastric mucosa were pre-incubated with peptides and glycoconjugates instead the pre-incubation of *H. pylori*.

IV. Results

In comparison to the control (untreated *H. pylori*), hydrolysates from human casein, camel casein and especially pea protein inhibited the adhesion of *H. pylori* to the gastric mucosa. With human milk casein peptides the adhesion could be reduced for more than 60%, with camel casein peptides for nearly 80%, and with peptides and glycoconjugates of pea proteins for even 95% in comparison to the control (see Table 1). The present results are indicative for the advantages to use pea protein hydrolysate and/or camel casein hydrolysate in the treatment and/or prevention of *H. pylori* infections and/or a disease associated with infection by *H. pylori* in mammals.

TABLE 1

| Ingredient | *H. pylori* adhesion (%) |
| --- | --- |
| Control | 100 |
| Hydrolysed bovine whey proteins | 100 |
| Hydrolysed bovine caseins | 100 |
| Hydrolyzed Human casein | 34 |
| Hydrolyzed Camel Casein | 21 |
| Hydrolyzed Pea protein | 5 |

The invention claimed is:

1. A method for the treatment of infection by gastrointestinal pathogens in mammals which comprises administering to a patient in need thereof an effective amount of a composition comprising pea protein hydrolysate, wherein the gastrointestinal pathogen is *Helicobacter pylori* (*H. pylori*).

2. The method of claim 1, wherein the composition comprises a lipid, a protein and a carbohydrate constituent wherein:
   the lipid constituent provides 5 to 50% of the total calories;
   the protein constituent provides 5 to 50% of the total calories;
   the carbohydrate constituent provides 15 to 90% of the total calories; and
   the protein constituent comprises: (i) pea protein hydrolysate, and (ii) at least one nitrogen source selected from the group consisting of milk proteins, milk protein hydrolysate, egg proteins, egg protein hydrolysate and mixtures thereof.

3. The method of claim 2, wherein the nitrogen source is selected from the group consisting of:
   (i) a nitrogen source comprising at least one milk protein selected from the group consisting of non-hydrolysed cows whey and non-hydrolysed cows casein,
   (ii) a nitrogen source comprising at least one milk protein hydrolysate selected from the group consisting of hydrolysed cows whey and hydrolysed cows casein, and
   (iii) any combination thereof.

4. The method of claim 2, wherein the carbohydrate constituent comprises a soluble, non-digestible, fermentable oligosaccharide.

5. The method of claim 1, wherein the osmolality of the composition is between 50 and 500 mOsm/kg.

6. The method of claim 1, wherein the composition is in the form of a nutritional or pharmaceutical composition.

* * * * *